United States Patent [19]

Reiniger

[11] 4,188,540
[45] Feb. 12, 1980

[54] X-RAY APPARATUS COMPRISING A WEIGHT COMPENSATION DEVICE

[75] Inventor: Friedrich Reiniger, Hamburg, Fed. Rep. of Germany

[73] Assignee: U.S. Philips Corporation, New York, N.Y.

[21] Appl. No.: 944,289

[22] Filed: Sep. 21, 1978

[30] Foreign Application Priority Data

Sep. 22, 1977 [DE] Fed. Rep. of Germany ....... 2742642

[51] Int. Cl.² ..................... G01N 21/00; G01N 23/00; G21K 5/06; G21K 5/08
[52] U.S. Cl. .............................. 250/439 R; 250/444; 269/323
[58] Field of Search ............... 250/439, 456, 521, 522, 250/523, 445 R, 446, 444; 269/322, 323

[56] References Cited

U.S. PATENT DOCUMENTS

| 3,916,203 | 10/1975 | Norgren | 250/439 |
| 3,933,251 | 1/1976 | Schmedemann | 250/439 |

Primary Examiner—Alfred E. Smith
Assistant Examiner—Thomas P. O'Hare
Attorney, Agent, or Firm—Thomas A. Briody; Edward J. Connors, Jr.; Jack E. Haken

[57] ABSTRACT

An X-ray apparatus, comprising a weight compensation device which is suspended from the ceiling and which includes a carriage which is displaceable along the ceiling. A component is displaceable along a patient table is suspended from the carriage by means of a cable. A signal from a transducer is applied to an electric motor which drives the carriage compensate for the relative displacement between the carriage and the suspended component.

5 Claims, 8 Drawing Figures

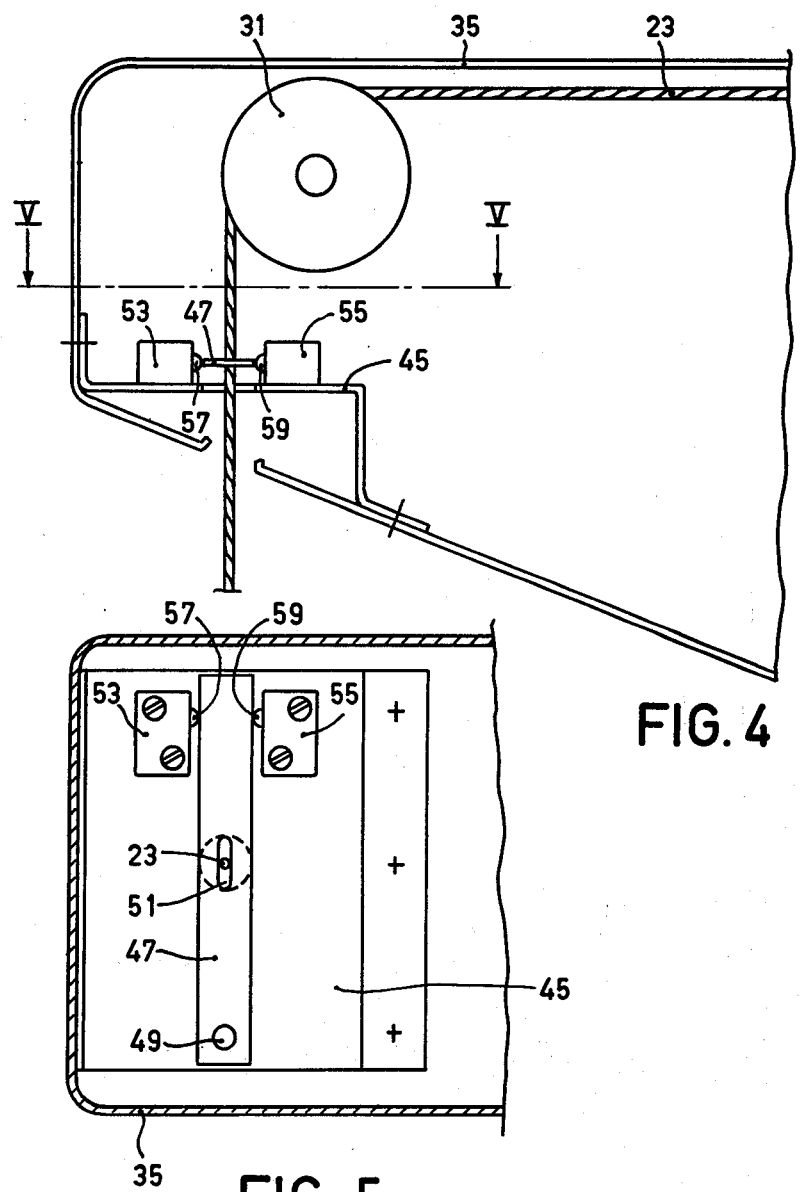

X-RAY APPARATUS COMPRISING A WEIGHT COMPENSATION DEVICE

The invention relates to an X-ray apparatus, comprising a weight compensation device which is suspended from a ceiling and which includes a carriage which is displaceable along the ceiling under the influence of an electric motor. Displaceable components (for example, an X-ray source and image detector) are suspended from said carriage on a flexible connecting cable.

BACKGROUND OF THE INVENTION

In a known X-ray apparatus of the described kind (German Pat. Spec. No. 736,294), the carriage can be freely displaced along the ceiling. The electric motor is mounted on the carriage, but does not drive the carriage only directly. The carriage searches for its new end position after of the patient table moves. Consequently, due to its mass inertia, the carriage is liable to travel beyond the desired position after which it returns to this position while jerking the cable as well as the X-ray source and image detector.

SUMMARY OF THE INVENTION

An object of the invention is to provide an X-ray apparatus in which jerking of the suspension cable is minimized. To this end, an X-ray apparatus in accordance with the invention comprises an electric motor which is operated by a control circuit which is connected to a transducer device which generates an output signal in reaction to relative displacement of the carriage with respect to the components suspended from the carriage. The electric motor operates as long as the relative displacement of the carriage from the suspended components deviates from a reference value. In the X-ray apparatus thus realized the component is brought into a desired end position by hand and the carriage is displaced to a position over the component by a follower control which compensates for the inertia of the carriage so that jerking of the cable due to overshoot of the carriage is avoided.

DESCRIPTION OF THE DRAWINGS

The invention will be described in detail hereinafter with reference to the accompanying diagrammatic drawings in which:

FIG. 4 is a cut-away front view of a first transducer for the X-ray apparatus shown in the preceding Figures;

FIG. 5 is a sectional view, taken along the line V—V, of the transducer shown in FIG. 4.

DESCRIPTION OF THE PREFERRED EMBODIMENTS

Figure 1:
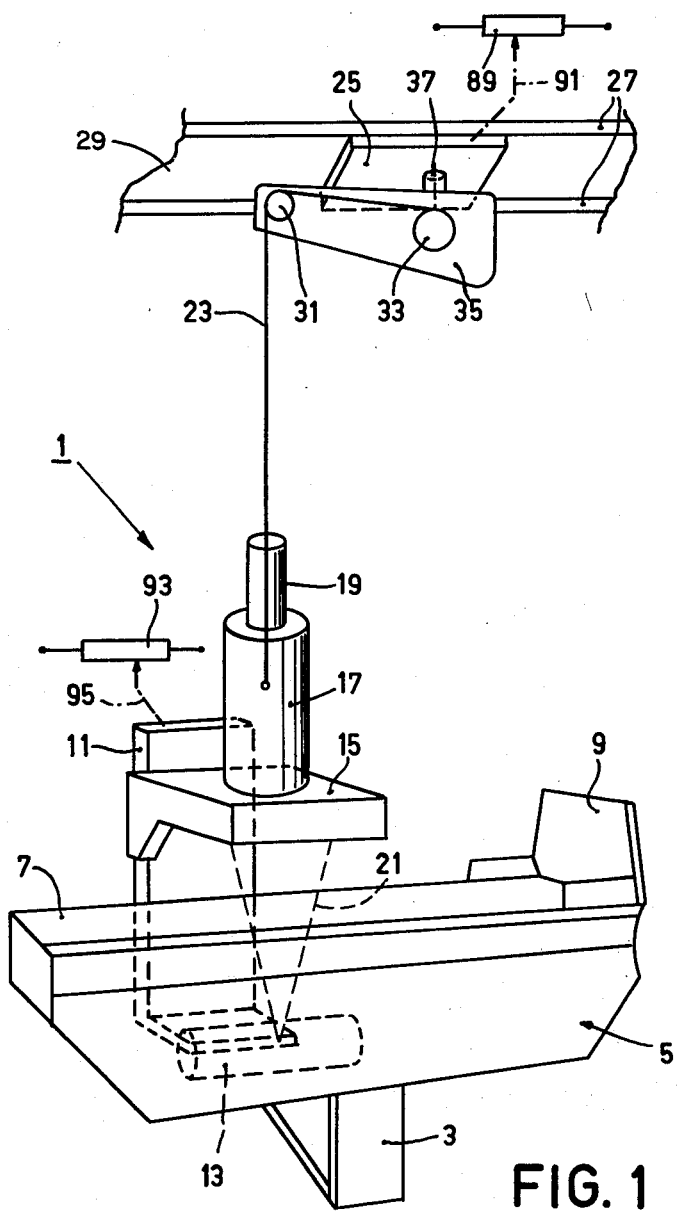
FIG. 1 is a perspective view of a part of an X-ray apparatus.

The X-ray apparatus 1 in FIG. 1 comprises a patient table 5 which is mounted on a base 3 and which is rotatable in a vertical plane. The patient table 5 comprises a top 7 with a foot support 9. A frame 11 is displaceable with respect to the table top 7 in a plane parallel to the top 7. An X-ray source 13, situated underneath the table top 7, is rigidly suspended from the frame 11. An X-ray film cassette 15, an X-ray image intensifier 17 and a television camera 19 are suspended from the frame 11 in a displaceable manner. The X-ray film cassette 15, the X-ray image intensifier 17 and the television camera 19 constitute an image detection device and are displaceable together along the frame 11 in a direction perpendicular to the table top 7. The X-ray beam emerging from the X-ray source 13 is denoted by the reference numeral 21. The weight of the X-ray film cassette 15, the X-ray image intensifier 17 and the television camera 19 is compensated for by a weight compensation device yet to be described. The weight of the X-ray source 13 is compensated for in known manner by a counterweight situated in the patient table 5. This counterweight may also be used to compensate for the weight of the frame 11. However, it is alternatively possible to provide compensation for the weight of the image detection device, as well as for the weight of the frame 11 and the X-ray source 13, near the ceiling 29.

Figure 2:
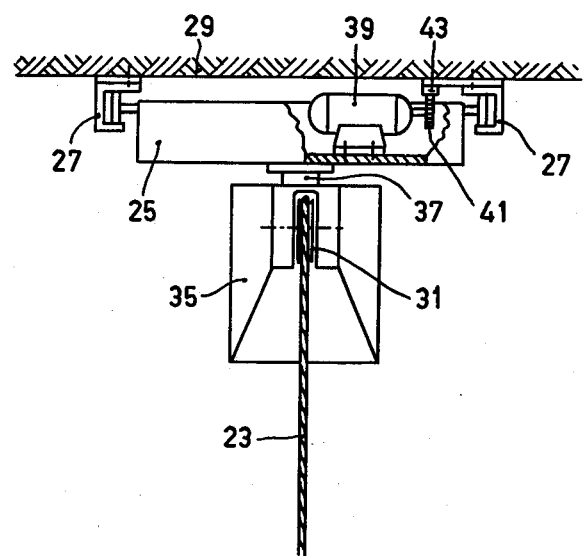
FIG. 2 is a side elevation of the drive for the carriage shown in FIG. 1.
Figure 3:
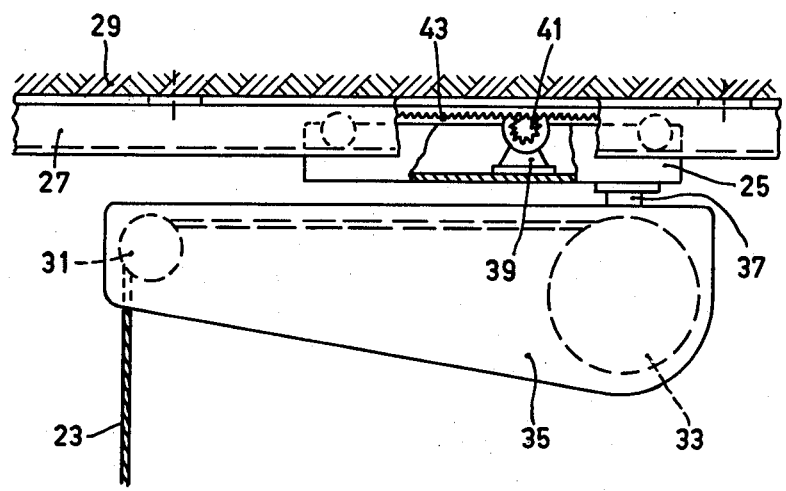
FIG. 3 is a front view of the drive for the carriage shown in FIG. 1.

The combination of X-ray film cassette 15, X-ray image intensifier 17 and television camera 19 is displaceable with respect to the frame 11 and is suspended from a carriage 25 on a flexible cable 23. The carriage 25 is displaceable along rails 27 connected to the ceiling 29. The cable 23 is supported on a guide roller 31 and a reel 33 which are rotatably journalled in a box 35. The reel 33 exerts a tensile force on the cable 23 which equals the weight of the image detection device. The force can be realized in a customary manner by means of a bias spring which acts on the reel 33 (not shown in FIGS. 1, 2 and 3). The reel 33 can also be driven by a motor. In that case, this motor can also produce the tensile force in cable 23 for weight compensation. The box 35 is rotatable about a vertical shaft 37 which is connected to the carriage 25. An electric motor 39 is mounted on the carriage 25 and drives a pinion 41 which engages a rack 43 secured to the ceiling 29. The pinion 41 can be driven clockwise as well as counter-clockwise by the electric motor 39. It is to be noted that the term "weight compensation device" is to be understood to mean the combination formed by the carriage 25, the carriage drive and the box 35.

The electric motor 39 is controlled by an output signal which is obtained from a transducer. The motor 39 is included in a control circuit which receives the output signal from the transducer.

In a first embodiment of an X-ray apparatus in accordance with the invention (see FIGS. 4 and 5) the transducer comprises an arm 47 which is arranged on a support 45 in the box 35 and which is pivotable about a pivot 49 mounted on the support 45. An opening 51 is provided at the approximate midpoint of the arm 47 wherethrough the cable 23 is passed. A first microswitch 53 is mounted on the support 45 to the left of the arm 47 near the end of the arm which is remote from the pivot 49. A second micro switch 55 is mounted on the support 45 to the right of the arm 47. Switch 53 comprises a sensor 57 which bears against arm 47 at the left while switch 55 comprises a sensor 59 which bears against arm 47 at the right. The switches 53 and 55 are switched off in the vertical position of the cable 23. In the case of a relative movement of the frame 11 to the left (see FIG. 1) with respect to the carriage 25, switch 53 is switched on, while in the case of a relative movement of the frame 11 to the right with respect to the carriage 25, switch 55 is switched on. Switches 53 and 55 are thus switched on when the cable 23 encloses an angle with a vertical line. This may also occur when the patient table 5 is not in the horizontal position and when the frame 11 is displaced along a patient table. The frame 11 may be displaced along the patient table by hand or alternatively, by means of a motor drive.

Figure 6:
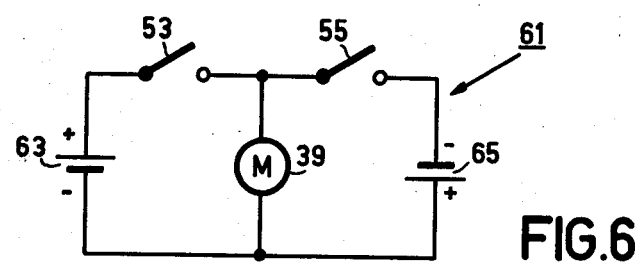
FIG. 6 is a control circuit for the transducer shown in FIGS. 4 and 5.

The switches 53 and 55 are included in a control circuit 61 (FIG. 6) which comprises power supply sources 63 and 65 of opposite polarity. Switch 53 is included in the connection between the power supply source 63 and the motor 39, while switch 55 is included in the connection between the power supply source 65 and motor 39. Motor 39 rotates as long as one of the switches 53 and 55 is switched on. Thus, follower control is obtained which prevents jerking of the cable 23, because the carriage 25 cannot overshoot beyond a position in which the cable 23 extends is vertical.

Figure 7:
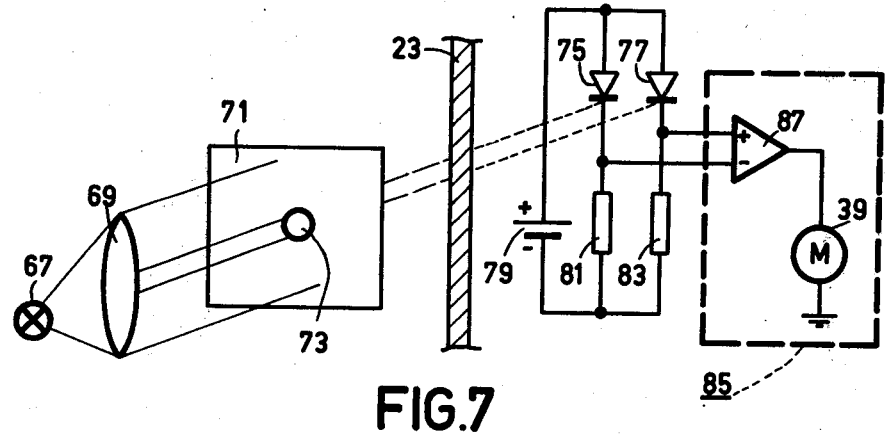
FIG. 7 is a second transducer device and control circuit used in an X-ray apparatus of FIGS. 1, 2 and 3.

In a second embodiment of an X-ray apparatus in accordance with the invention (see FIG. 7), the transducer comprises a light source 67 which is directed on an aperture 71 by a lens 69. The aperture 71 comprises a round opening 73 having a diameter equal to or slightly larger than the diameter of the cable 23. The transducer furthermore comprises two photodiodes 75 and 77 which are symmetrically situated with respect to the opening 73. The cable 23 in its vertical position is present between the opening 73 and the photodiodes 75 and 77 and completely shields the photodiodes 75 and 77. The photodiodes 75 and 77 are connected to a common power supply source 79 and resistors 81 and 83, respectively. If the cable 23 assumes a position which deviates from the vertical one of the photodiodes is exposed more to the light from the source 67 than the other diode. The output signals of the two photodiodes are applied to a control circuit 85 which includes a comparator in the form of a differential amplifier 87. The output signal of the differential amplifier 87 is applied to the electric motor 39. The direction of rotation of the electric motor 39 is dependent of the polarity of the output signal of the differential amplifier 87. The motor 39 rotates as long as the cable 23 is not vertical. The electro-optical transducer can be connected to the box 35 or to the frame 11.

Figure 8:
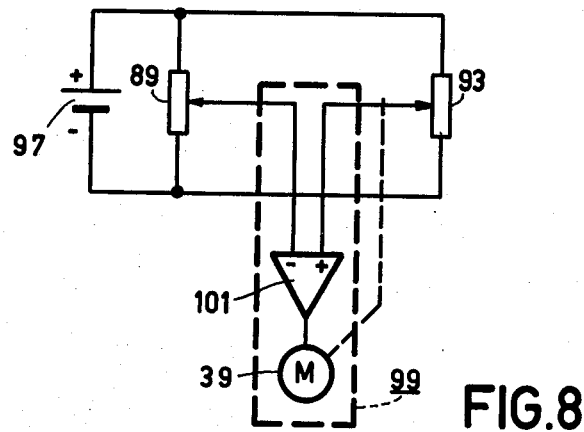
FIG. 8 is a third transducer device and control circuit for the X-ray apparatus of FIGS. 1, 2 and 3.

In a third embodiment of an X-ray apparatus in accordance with the invention (diagrammatically shown in FIG. 1 for the sake of brevity), the transducer device comprises a first potentiometer 89 whose wiper 91 is connected to the carriage 25, and a second potentiometer 93 whose wiper 95 is connected to the frame 11. The bodies of the potentiometers are maintained in a fixed frame of reference. The wipers 91 and 95 are thus related to the position of the weight compensation device and the frame 11, respectively. The difference between the output signals from the potentiometers 89 and 93, therefore, is a measure for the deviation of the cable 23 from its vertical position. In FIG. 8 the output signals of the potentiometers 89 and 93, powered by a power supply source 97, are applied to a control circuit 99, which may be to a comparator in the form of a differential amplifier 101. The differential amplifier 101 is connected to the electric motor 39, so that follower control is obtained.

In apparatus in which the patient table 5 is always in the horizontal position the potentiometer 93 may be linear potentiometer. If the patient table is rotatable about a horizontal axis in the base 3 a cosine potentiometer is used, so that the output signal to the control circuit is compensated for as regards the position of the patient table 5.

In the embodiment described with reference to the FIGS. 4 and 5, the arm 47 cooperates with two microswitches. However, the arm 47 may alternatively be coupled to the wipers of potentiometers which supply the desired output signal.

Because the box 35 is rotatable about the shaft 37, the described follower system can also be extended with an analog system which is capable of compensating for movements of a frame 11 which is also displaceable in a direction transverse to the longitudinal direction of the rails 27. In that case the carriage 25 is also displaceable in a direction transverse to the rails 27.

What is claimed is

1. In X-ray apparatus of the type which includes a carriage which is suspended from and displaceable along a ceiling; motor means which function to displace said carriage along said ceiling; a flexible connecting member having a first end attached to said carriage; and a displaceable component suspended from a second end of said flexible member, the improvement comprising:
    transducer means which generate an output signal which represents a relative horizontal displacement between the carriage and the displaceable component and
    control circuit means which receive the output signal from the transducer and operate the motor means to decrease said relative displacement whenever said relative displacement exceeds a reference value.

2. The improvement claimed in claim 1 wherein the transducer means comprise:
    a position detector means connected to the carriage and
    a pivotable arm which couples the position detector to the flexible connecting member; and wherein said position detector means functions to supply a signal which is representative of the angle enclosed between the connecting member and a vertical line.

3. The improvement claimed in claim 2 wherein the position detector means comprise a first switch and a second switch;
    said pivotable arm being disposed to operate said first switch when rotated in a first direction and to operate said second switch when rotated in a second opposite direction;
    said first switch functioning, when operated, to supply said motor means from a first polarity power source and said second switch functioning, when operated, to supply said motor means from a second, opposite polarity power source.

4. The improvement claimed in claim 1 wherein the transducer means comprises:
    a stationary light source disposed on one side of the connecting member;
    two stationary optical-electrical converters disposed opposite the light source on an opposite side of the connecting member; and wherein
    the control circuit means comprise comparator means connected to receive signals from the optical-electrical converters and to supply power to the motor means in response thereto.

5. Apparatus of claim 1 wherein the transducer means comprise:

a first potentiometer connected to produce a first output signal which is a measure of the position of the carriage with respect to a fixed frame of reference;

a second potentiometer connected to produce a second output signal which is a measure of the position of the displaceable component with respect to said frame of reference; and the control circuit means comprise comparator means which receives signals from the potentiometers at its inputs and supplies power to the motor means in response thereto.

* * * * *